US008642081B2

(12) United States Patent
Olsen et al.

(10) Patent No.: US 8,642,081 B2
(45) Date of Patent: Feb. 4, 2014

(54) CHEWABLE, SUCKABLE AND SWALLOWABLE TABLET CONTAINING A CALCIUM-CONTAINING COMPOUND AS AN ACTIVE SUBSTANCE

(75) Inventors: Peder M. Olsen, Kirke Hyllinge (DK); Karin L. Christensen, Frederiksberg (DK); Dina W. Sørensen, Slagelse (DK)

(73) Assignee: Takeda Nycomed AS, Asker (NO)

( * ) Notice: Subject to any disclaimer, the term of this patent is extended or adjusted under 35 U.S.C. 154(b) by 377 days.

(21) Appl. No.: 11/628,406

(22) PCT Filed: May 24, 2005

(86) PCT No.: PCT/DK2005/000337
§ 371 (c)(1),
(2), (4) Date: Oct. 16, 2007

(87) PCT Pub. No.: WO2005/117829
PCT Pub. Date: Dec. 15, 2005

(65) Prior Publication Data
US 2008/0069877 A1 Mar. 20, 2008

(30) Foreign Application Priority Data
Jun. 1, 2004 (DK) .................................. 2004 00860

(51) Int. Cl.
*A61K 9/20* (2006.01)
(52) U.S. Cl.
USPC ........................................................ 424/465
(58) Field of Classification Search
USPC ........................................................ 424/465
See application file for complete search history.

(56) References Cited

U.S. PATENT DOCUMENTS

| | | | |
|---|---|---|---|
| 4,684,534 A | 8/1987 | Valentine | |
| 4,720,378 A * | 1/1988 | Forse et al. | 424/10.2 |
| 4,882,161 A * | 11/1989 | Scheurer et al. | 424/441 |
| 5,405,623 A * | 4/1995 | Barkalow et al. | 426/5 |
| 6,149,941 A | 11/2000 | Schwarz et al. | |
| 6,256,963 B1 | 7/2001 | Kim et al. | |
| 2002/0193355 A1 | 12/2002 | Meignant et al. | |
| 2004/0071772 A1 | 4/2004 | Narita et al. | |

FOREIGN PATENT DOCUMENTS

| | | |
|---|---|---|
| DE | 19617487 A1 | 11/1997 |
| DE | 20216314 U1 | 12/2003 |
| EP | 0647591 A1 | 4/1995 |
| EP | 0 872 240 A | 10/1998 |
| EP | 0914818 A1 | 5/1999 |
| EP | 1369131 A1 | 12/2003 |
| FR | 2 724 844 A | 3/1996 |
| JP | 5306229 A | 11/1993 |
| JP | 5306229 A | 11/1993 |
| JP | 2001-316249 A | 11/2001 |
| JP | 2002-529496 A | 9/2002 |
| WO | WO-92/10168 A1 | 6/1992 |
| WO | WO-95/08273 | 3/1995 |
| WO | WO-95/08273 A1 | 3/1995 |
| WO | WO-96/09036 A1 | 3/1996 |
| WO | WO-97/41835 A1 | 11/1997 |
| WO | WO-97/47287 A1 | 12/1997 |
| WO | WO-99/06051 A1 | 2/1999 |
| WO | WO-00/28973 | 5/2000 |
| WO | WO-00/28973 A1 | 5/2000 |
| WO | WO-03/055500 | 7/2003 |
| WO | WO-2005/032944 | 4/2005 |

OTHER PUBLICATIONS

Hancock et al, The Relative Densities of Pharmaceutical Powders, Blends, Dry Granulations, and Immediate-Release Tablets, Pharmaceutical Technology, Apr. 2003, pp. 64-80.*
Overgaard et al., Patients' evaluation of shape, size, and colour of solid dosage forms, Pharmacy World & Science, vol. 23, No. 5, pp. 185-188, 2001.*
NeosorbP100T product specification, http://www.signetchem.com/pdf/Roquette/Neosorb%20P%20100%20T.pdf—accessed Jun. 22, 2009).*
"2.9.3. Dissolution Test for Solid Dosage Forms" European Pharmacopoeia 7.0 pp. 256-263 Jan. 2010:20903 corrected 6.8, 2010.
"2.9.7. Friability of Uncoated Tablets" European Pharmacopoeia 7.0 p. 266 Jan. 2010:20907, 2010.
"2.9.1. Disintegration of Tablets and Capsules" European Pharmacopoeia 7.1 pp. 3331-3332 Apr. 2011:20901, 2011.
"2.9.8. Resistance to Crushing of Tablets" European Pharmacopoeia 7.0 p. 267 Jan. 2008:20908, 2008.
Klobes p. et al. "Porosity and Specific Surface Area Measurements for Solid Materials" NIST, (SP 960-17), 2006.

* cited by examiner

*Primary Examiner* — Frederick Krass
*Assistant Examiner* — Adam C Milligan
(74) *Attorney, Agent, or Firm* — Edwards Wildman Palmer LLP; Peter F. Corless; Christine C. O'Day

(57) ABSTRACT

The present invention relates to a nutriceutical and/or pharmaceutical composition for oral use containing a calcium-containing compound. The composition is in the form of tablets that are designed so that they have an acceptable taste and mouthfeel, whereby the tablets are chewable or suckable, and at the same time the tablets fulfill the requirements with respect to technical properties in order to ensure that the tablets can be dispensed by means of a dose-dispensing machine. In a preferred embodiment, the tablet comprises calcium carbonate and sorbitol with a mean particle size of 38 or 110 microns. In another embodiment, the tablets comprise calcium carbonate and Vitamin D as active ingredients.

37 Claims, 4 Drawing Sheets

Figure 1:
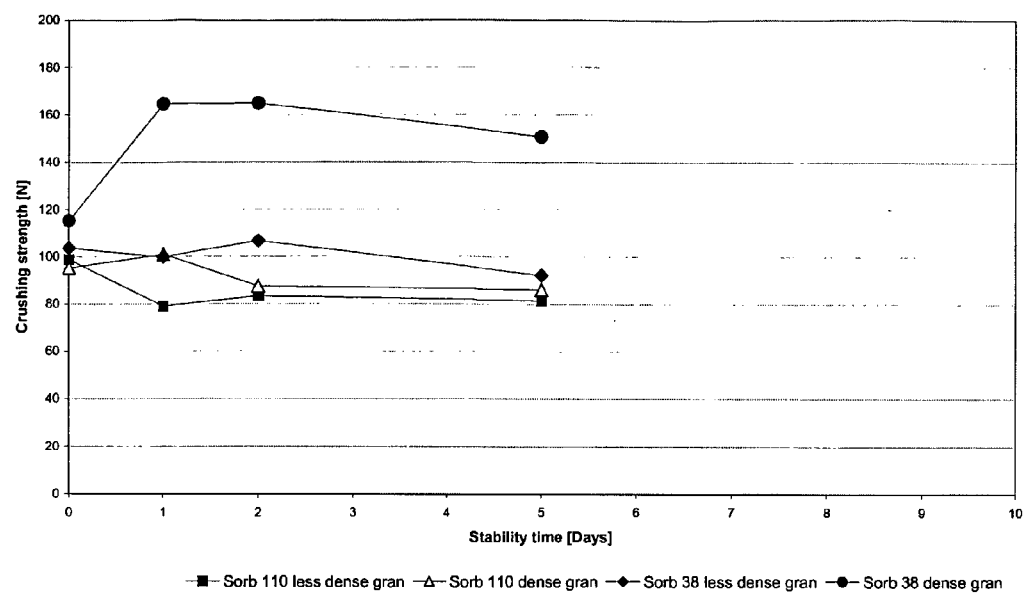

CHEWABLE, SUCKABLE AND SWALLOWABLE TABLET CONTAINING A CALCIUM-CONTAINING COMPOUND AS AN ACTIVE SUBSTANCE

FIELD OF THE INVENTION

The present invention relates to a nutriceutical and/or pharmaceutical composition for oral use containing a calcium-containing compound. The composition is in the form of tablets that are designed so that they have an acceptable taste and mouthfeel, whereby the tablets are chewable or suckable, and at the same time the tablets fulfil the requirements with respect to technical properties in order to ensure that the tablets can be dispensed by means of a dose-dispensing machine.

BACKGROUND OF THE INVENTION

In today's world the global healthcare area faces major changes. The future holds further medical advancement with an increasing elderly population demanding extended care. To improve compliance for e.g. the elderly population, packing of medicine in daily unit/multiple dose packages ("dose dispensing") is implemented in more and more countries such as, e.g., European countries. Typically the medicine is dosed for a two weeks period of time and the daily dose package contains e.g. packages/bags for the morning, noon, evening and night medication. On each bag information about the person and the medicine are printed.

Development of tablets that are sufficiently robust to be dispensed via a dose-dispensing machine is a particular challenge when the tablets are formulated as chewable tablets. Normally, chewable tablets do not have sufficient technical properties, which are required for a dose-dispensing machine (e.g. the tablets are too fragile and when exposed to the filling equipment they afford dust which makes the filling difficult or impossible). Today no product is available on the market containing a calcium-containing compound as a therapeutically and/or prophylactically active substance and being chewable, i.e. having an acceptable taste and mouthfeel, and at the same time having sufficient technical properties to enable dispensing via a dose-dispensing machine. Accordingly, it is not possible for patients to obtain a daily dose package packed by a dose-dispensing machine, which package includes one or more calcium-containing chewable tablets. The present inventors address this issue by providing a tablet that is sufficient robust to withstand packaging by a dose-dispensing machine and at the same time gives the patient or the user the liberty of choosing whether she wants to chew, suck and/or swallow the tablet, i.e. the improved technical properties do not impair an acceptable taste and mouthfeel.

DESCRIPTION OF THE INVENTION

As mentioned above, there is a need for developing improved pharmaceutical composition comprising a calcium-containing compound, which composition is suitable for packaging via a dose-dispensing machine and at the same time is chewable. To the best of the inventor's knowledge such a composition is not available today most likely because chewing tablets with a calcium-containing compound must fulfil very high requirements with respect to the sensory properties including taste and mouthfeel. In fact, it has previously been described that the quality of the calcium-containing compound as well as the method for preparation of a pharmaceutical composition containing the calcium-containing compound are of great importance in order to obtain acceptable taste and mouthfeel of a chewable tablet (WO 00/28973). The method described in WO 00/28973 relates to a fluid-bed process, whereby granulate is obtained for manufacturing of tablets that have suitable sensory properties. However, such tablets do not possess the necessary mechanical strength to withstand exposure to filling via a dose-dispensing machine. Furthermore, a fluid-bed process often lead to a very porous granulate, between 20% and 30%, which in turn lead to porous tablets, i.e. in the present context such tablets may be too large to fit into the cassettes of the dose-dispensing machines. The pharmaceutically acceptable sugar alcohol employed according to the invention has a mean particle size of at the most about 150 μm such as, e.g., at the most about 110 μm, at the most about 100 μm, at the most about 90 μm, at the most about 80 μm, at the most about 70 μm, at the most about 60 μm, at the most about 50 μm such as, at the most about 40 μm, at the most about 20 μm such as, e.g. about 10 μm. In a specific embodiment, the pharmaceutically acceptable sugar alcohol employed has a mean particle size in a range of from about 5 to about 150 μm such as, e.g., from about 5 to about 110 μm or from about 5 to about 80 μm.

Also, in order to enable a good patient compliance even in those situations where e.g. a chewing tablet is swallowed, the present inventors have aimed to developing a tablet that fulfils all requirements with respect to chewable tablets, suckable tablets and swallowable tablets. In the present context, chewable tablets include crunchable tablets. Normally, the requirements with respect to chewable tablets are in direct contrast to the requirements of swallowable tablets (e.g. chewable tablets should not disintegrate but "melt" on the tongue, whereas swallowable tablets are much more robust, but must fulfil requirements with respect to disintegration and dissolution of the active ingredient). Furthermore, chewing tablets normally do not fulfil a requirement with respect to stability that is relevant and set by national regulatory authorities with respect to tablets dispensed by a dose-dispensing machine. This requirement is that the tablets must be stable when stored outside the packing i.e. in an open petri dish at 25° C. and 60% relative humidity (RH) for 1 month. The known chewing tablets containing a calcium-containing compound become grey or stained upon storage and, in general, cannot fulfil the above requirements.

The present inventors have solved this problem by providing a tablet that comprises a calcium-containing compound as an active substance, the tablet having properties that are suitable for dispensing via a dose-dispensing machine, and the tablet has an acceptable taste and mouthfeel when tested by a professional/skilled sensory test panel of at least 6 test persons. In the present context, a professional/skilled sensory test panel denotes test persons that have the ability or have been trained to have the ability of evaluating taste and mouthfeel of ingestible products.

Furthermore, i) the high dose of calcium carbonate (normally 300-600 mg of elemental calcium twice daily, corresponding to 750-1500 mg of calcium carbonate twice daily), ii) the inherent poor properties of regular shaped calcium carbonate with respect to tabletting properties like compressibility, which accordingly calls for the need of adding one or more pharmaceutically acceptable excipients in order to obtain a suitable compressibility, and iii) the extremely bad taste or mouthfeel of a calcium salt itself especially with respect to chalkiness make it very difficult to prepare a tablet that has a suitable small size, which is conveniently small for a patient. Sufficient taste masking is another major challenge when formulating chewable tablets.

With an aim of preparing a smaller tablet that still has acceptable taste and mouthfeel, the present inventors have found that the use pharmaceutically acceptable sugar alcohols as binding material in the agglomeration process is particularly suitable. To this end the present inventors have found that when a regularly shaped calcium-containing compound is used, which has very poor compressibility properties itself, then—in order to obtain an acceptable end result it is important to use a pharmaceutically acceptable sugar alcohol having a particle size (D(v; 0.5) below 150 μm resulting in a tablet having a porosity below 20%. In a preferred embodiment using a roller compacted composition containing a calcium-containing compound it is very important that the sugar alcohol used also has a micro structure, i.e. a structure that enables a certain deformation e.g. during compaction process in order to establish sufficient bonding between the individual calcium (and sugar alcohol) particles Accordingly, the invention relates to a calcium-containing tablet suitable for dispensing via a dose-dispensing machine, the tablet comprising a regularly shaped calcium-containing compound as an active substance and a pharmaceutically acceptable sugar alcohol having a micro structure, which tablet is stable when tested in an open petri dish at 25° C. and 60% relative humidity (RH) for 1 week or more such as, e.g., for 2 weeks or more, for 3 weeks or more, for 4 weeks or more, for 1 month or more, for 2 months or more, or for 3 months or more.

In the present context, the term "regularly shaped" in connection with a calcium-containing compound is intended to denote that the individual particles as have a rounded or smooth-like surface like e.g. cubic-formed crystals. The regular shape results in a relatively low specific surface area that is below 1.5 m$^2$/g In the present context, the term "micro structure" used in connection with sugar alcohols is intended to denote that a single crystal of the sugar alcohol is a polycrystal such as multiple crystals or fiber crystals comprising smaller units, i.e. the crystals have an identifiable substructure that is detectable by SEM. The micro structure enables a certain deformation and sufficient distribution throughout the tablet during the roller compaction process in order to establish sufficient bonding between the individual calcium (and sugar alcohol) particles.

The present invention is based on the findings that the use of particular qualities of sugar alcohols in tablets lead to tablets that are stable when stored in open petri dishes as described above.

Furthermore, when chewable tablets are prepared, the tablets must not be so hard, i.e. have an unacceptable high crushing strength, so that it becomes difficult for a patient to chew. Accordingly, it is important to balance the crushing strength to an acceptable level. The present inventors have found that it is possible to determine whether a specific sugar alcohol is suitable for use in the preparation of a particulate material according to the invention by subjecting the sugar alcohol to two tests, namely i) a SEM photo showing that the sugar alcohol has a micro structure and ii) a test showing the compressibility properties of the sugar alcohol itself. To this end, the pharmaceutically acceptable sugar alcohol—when compressed into tablets containing 100% w/w of the sugar alcohol using 11.29 mm flat faced punches and a max compression force of 25 kN—has a slope of correlation between crushing strength (measured in N) and compression pressure (measured in N) of $7 \times 10^{-3}$ or more, when tested using a Schleuniger Hardness Autotester 4 or Schleuniger Tablet tester 6D and a tablet placed with the longest dimension orthogonal to the jaws of the crushing strength apparatus.

Moreover, in contrast to what is general knowledge within the field of pharmaceutical formulation, the present inventors have found that a sugar alcohol like sorbitol is not suitable for use in the standard quality generally recommended. This quality has a mean particle size of about 300 μm, but such a mean particle size is too large in order to enable a sufficient distribution of sorbitol particles around the particles of the calcium-containing compound resulting in tablets having unacceptable properties with respect to crushing strength. The particle size of e.g. sorbitol must be much smaller in order to obtain good and acceptable results with respect to crushing strength.

Accordingly the pharmaceutically acceptable sugar alcohol employed has a mean particle size of at the most about 150 μm such as, e.g., at the most about 110 μm, at the most about 100 μm, at the most about 90 μm, at the most about 80 μm, at the most about 70 μm, at the most about 60 μm, at the most about 50 μm such as, at the most about 40 μm, at the most about 20 μm such as, e.g. about 10 μm.

In specific embodiment the pharmaceutically acceptable sugar alcohol employed has a mean particle size in a range of from about 5 to about 150 μm such as, e.g., from about 5 to about 110 μm or from about 5 to about 80 μm.

Furthermore, it would have been expected that use of e.g. sorbitol in a much smaller particle size would lead to stability problems as it is known that sorbitol is hygroscopic and a smaller particle size increases the surface area and thereby the risk of adsorbing moisture e.g. from the surroundings. However, as demonstrated herein, tablets prepared using a granulate obtained by roller compaction of a composition containing the calcium-containing compound and e.g. sorbitol having a mean particle size well below 300 μm are stable with respect to crushing strength, i.e. the crushing strength of the tablets when stored in open petri dishes at 25° C. and 60% RH changes at the most 50% such as, e.g. at the most about 40%, at the most about 30%, at the most about 20%, at the most about 15%, at the most about 10% during a time period that starts after 5 days of storage in open petri dishes and runs during the remaining storage period which is 90 days.

Such improved stability indicates that products obtained as described herein are suitable for so-called zone 3 or 4 (ICH Q1F), i.e. countries that have a relatively high average temperature and relative humidity.

In order to ensure a sufficient distribution of the pharmaceutically acceptable sugar alcohol between the individual particles of the calcium-containing compound e.g. during the roller compaction, the inventors have found that the binder suitably have a mean particle size of at the most about 150 μm such as, e.g., at the most about 110 μm, at the most 100 μm, at the most about 90 μm, at the most about 80 μm, at the most about 70 μm, at the most about 60 μm, at the most about 50 μm, at the most 40, at the most 20 such as, e.g. about 10 μm.

In the literature (see Pharmaceutical Technology, volume 1 (tabletting technology), Michael H. Rubinstein (ed.), Ellis Horwood Ltd, 1987) it has been stated that sorbitol has good tabletting properties and that the admixing of this excipient will increase the tablet strength. However, it has also been stated that in order to get this effect the sorbitol should be of the "instant" quality that is manufactured by spray-drying. The optimal particle size of sorbitol "instant" has been described as having 60-90% between 212-500 μm when determined by sieve analysis. The recommended concentration in the tablet is 30-80%. However, in the context of the present invention, sorbitol can be used as a binder (having sweetening properties) in tablets.

Especially two sugar alcohols have proved to be suitable for use in the roller compaction based agglomeration process, namely sorbitol and isomalt. However, it is contemplated that other sugar alcohols also may be available in a quality that fulfils the above-mentioned criteria, and such sugar alcohols are envisaged to be suitable for use according to the invention. Below is mentioned other sugar alcohols, that may fulfil the above-mentioned criteria.

In a specific embodiment, the sugar alcohol is sorbitol, notable a sorbitol that has a mean particle size in a range of from about 25 to about 50 µm such as, e.g., from about 35 to about 45 µm.

In another embodiment, the sugar alcohol is isomalt, notably an isomalt that has a mean particle size in a range of from about 20 to about 50 µm such as, e.g., from about 25 to about 35 µm.

Sugar alcohols according to the invention are typically selected from the group consisting of mannitol, xylitol, maltitol, inositol, and lactitol, and mixtures thereof. Specific qualities of sorbitol and isomalt that do not fulfil the above-mentioned criteria may of course also be added. Examples are Sorbitols, Neosorb P100T, Sorbidex P166B0 and Sorbogem Fines Crystalline Sorbitol available from Roquette Freres, Cerestar and SPI Polyols Inc. respectively. Maltisorb P90 (maltitol) available from Roquette Freres, Xylitol CM50, Fructofin CM (fructose) and Lactitol CM50 available from Danisco Sweeteners, Isomalt ST-PF, Gaio Tagatose and Manitol available from Palatinit, Arla Foods and Roquette, Freres respectively. Further examples of suitable saccharide-based binders/sweeteners include sucrose, dextrose.

In a specific embodiment, a tablet according to the invention may comprise a mixture of sorbitol and xylitol. In such cases, the weight ratio between sorbitol and xylitol is normally in a range of from about 1:0.1 to about 1:1.5 such as, e.g., about 1:1. A mixture of isomalt and xylitol is also suitable and in such cases, the weight ratio between isomalt and xylitol is normally in a range of from about 1:0.1 to about 1:1.5 such as, e.g., about 1:1.

In a paragraph given in the following, a description of calcium-containing compounds is given. However, as mentioned herein before, the calcium-containing compound for use according to the invention has a regular shape such as a calcium salt like calcium carbonate in specific qualities. In preferred aspect, the calcium salt is calcium carbonate and notably with a shape and a mean particle size corresponding to that of Scoralite 1B or Merck 2064. In a specific embodiment, the calcium carbonate is Scoralite 1B or Merck 2064.

However, the above-mentioned calcium carbonate may be used in admixture with other calcium-containing compounds such as, e.g., those mentioned herein in the following paragraph, especially calcium citrate, calcium lactate, calcium phosphate including tricalcium phosphate, calcium gluconate, bisglycino calcium, calcium citrate maleate, hydroxyapatite including solvates, and mixtures thereof.

Normally, the content of the regularly shaped calcium-containing compound in the tablet is in a range of from about 40% to about 95% w/w such as, e.g., from about 45% to about 95% w/w, from about 50% to about 95% w/w, from about 55% to about 90% w/w or at least about 60% w/w, at least about 65% w/w, at least about 70% w/w or at least about 75% w/w.

Due to a careful selection of the calcium-containing compound and the sugar alcohol in combination with one or more suitable pharmaceutically acceptable excipients it has been possible to obtain a tablet that has a suitable taste and mouthfeel.

Accordingly, it has been possible to obtain a tablet that is stable towards storage in an open petri dish at 25° C. and 60% relative humidity (RH) for 1 week or more such as, e.g., for 2 weeks or more, for 3 weeks or more, for 4 weeks or more, for 1 month or more, for 2 months or more, or for 3 months or more, i.e. it is possible to met the regulatory requirements with respect to stability in order to be dispensed by a dose-dispensing machine.

A tablet according to the invention is also stable towards storage in a closed container e.g. it is stable at 25° C. and 60% RH for 6 months or more such as, e.g. for 8 months or more, for 10 months or more, for 1 year or more, for 1.5 years or more or for 2 years or more or for 5 years or more and/or it is stable towards storage in a closed container at 30° C. and 65% RH for 2 months or more such as, e.g., for 4 months or more, for 6 months or more, for 1 year or more and/or it is stable towards storage in a closed container at 40° C. and 75% RH for 1 month or more such as, e.g., for 2 months or more or for 3 months or more, or for 6 months or more, i.e. it is possible to meet the standard regulatory requirements with respect to stability.

With respect to stability, the following parameters are of importance:
i) crushing strength,
ii) friability,
iii) appearance and/or
iv) water sorption As mentioned above, normally, chewing tablets cannot fulfil the above-given requirements. Moreover, the tablets according to the invention are also designed so that they can be swallowed. This requires that the tablets also fulfil specific requirements with respect to disintegration and dissolution, i.e. the requirements with respect to tablets that give the patient the liberty of choosing how she want to intake the tablet (i.e. by chewing, sucking or swallowing) are much more demanding compared to tablets that are intended e.g. for swallowing.

Accordingly, the tablets should also be stable with respect to
v) disintegration, and
vi) dissolution.

However, the most challenging task in this respect is to formulate tablets, which are designed to give the person in need thereof the liberty of choosing between chewing, sucking or swallowing, because it is almost impossible to formulate tablets that fulfils requirements to disintegration and dissolution without using any disintegrating agent. In general, chewing tablets are formulated without any need for a disintegration agent, which is an advantage as disintegrating agents contribute to an unpleasant taste or mouthfeel. Therefore, formulation of tablets containing one or more disintegrating agents and which have a good taste and an acceptable mouthfeel is not a straightforward or easy task for a person skilled in the art.

The crushing strength and the friability are important in order to ensure that the tablets are sufficiently robust to withstand dispensing by a dose-dispensing machine. Furthermore, in the present context, the crushing strength and the friability should not markedly change during the storage period. If the crushing strength becomes too high it is difficult for the patient to chew the tablets, if it is too low, the tablet breaks or disintegrates and if the friability is too high, the tablets are fragile and too must dust will appear during the filling by the dose-dispensing machine or during the normal handling of the tablets e.g. by the patients.

Accordingly, the present invention provides tablets that have a crushing strength in a range of from about 40 to about 150 N such as, e.g., from about 50 to about 140 N, from about 60 to about 140 N or from about 70 to about 140 N. The crushing strength of the tablets at the most changes 50% such as, e.g., at the most about 40%, at the most about 30%, at the most about 20%, at the most about 15%, at the most about 10% or at the most about 5% during a time period that starts after 5 days of storage and runs during the remaining storage period, i.e. at least 1 week. In the present context the term "after x days of storage" is intended to denote x days after storage at the stated conditions, and the term "storage period" is intended to denote storage at given conditions for a given period of time.

Moreover, the friability of the tablets is at the most about 5% such as, e.g., at the most about 4%, at the most about 3%, at the most about 2%, at the most about 1%, at the most about 0.5% or at the most about 0.1% during the storage period, and/or the friability of the tablets at the most changes 50% such as, e.g., at the most about 40%, at the most about 30%, at the most about 20%, at the most about 15%, at the most about 10% or at the most about 5% during a time period that starts after 5 days of storage and runs during the remaining storage period.

Another stability issue is chipping that also can be avoided or improved by the present invention With respect to appearance, this is tested by visual inspection of the tablets. The tablets are said to be stable if no discoloration or greyish colour appear on the surface of the tablet or if no staining is visible during the test period (storage period).

As mentioned above, the tablet according to the invention should not sorb water to a large extent. Therefore, the water sorption of the tablet is at the most about 5% at 25° C. and 60% RH such as, e.g. at the most about 4%, at the most about 3%, at the most about 2%, at the most about 1%, at the most about 0.5% or at the most about 0.1%. Moreover, water sorption of the tablet at 25° C. and 60% RH at the most changes 50% such as, e.g., at the most about 40%, at the most about 30%, at the most about 20%, at the most about 15%, at the most about 10% or at the most about 5% during the storage period. The water sorption is measured by a dynamic water sorption method.

As mentioned above, there are specific requirements that must be fulfilled when the tablets are swallowable. These requirements ensure that the active substance is available for absorption upon administration and that any change in availability does not arise from changes in the tablets upon storage. The requirement to disintegration time ensures that the tablet disintegrates into small particles and the requirement to dissolution time ensures that the active substance is release from the tablet and can be dissolved in the surrounding fluid. Accordingly, a tablet according to the invention has a disintegration time—determined according to Ph. Eur.—of at the most about 30 min such as, e.g. at the most about 15 min. In contrast to normal chewing tablets, the tablets according to the invention may be coated with a very thin hydrophilic coating. In those cases where the tablets are coated, the disintegration time may be at the most 30 min, whereas the disintegration time for uncoated tablets is normally at the most 15 min.

The disintegration time is stable upon storage and accordingly, the disintegration time changes at the most 50% such as, e.g., at the most about 40%, at the most about 30%, at the most about 20%, at the most about 15%, at the most about 10% or at the most about 5% during a time period that starts after 5 days of storage and runs during the remaining storage period.

With respect to dissolution time, at least 50% w/w such as, e.g., at least 60% w/w at least about 70% w/w, at least about 75% w/w or at least about 80% w/w of the calcium-containing compound is released within at the most about 2 hours such as, e.g., at the most about 1.5 hour, at the most about 1 hour, at the most about 45 min or at the most about 30 min. Furthermore, the dissolution time—measured as the time for 60% w/w of the calcium-containing compound to be released in a dissolution test according to USP—changes at the most 50% such as, e.g., at the most about 40%, at the most about 30%, at the most about 20%, at the most about 15%, at the most about 10% or at the most about 5% during a time period that starts after 5 days of storage and runs during the remaining storage period.

As appears from the above, the present invention solves the problem of providing chewing tablets with an acceptable taste (which tablets also may be sucked or swallowed) and with mechanical properties and a size that are suitable for use when the tablets are dispensed by a dose-dispensing machine.

In general, improved outcomes and reduced costs are some of the advantages in applying a dose-dispensing machine, which may be achieved by, e.g., i) reduced distribution time, which increases staff efficiency and releases staff to other functions, ii) reduced incidence of prescribing, dispensing and/or administration errors, iii) improved patient care by clearly labelled unit/multi dose packages, which help patients receiving the right medication at the right time, and/or iv) reduced waste of medicine.

As mentioned above, the regulatory requirements for tablets dispensed by a dose-dispensing machine are relative high, and they may be different from country to country with regard to the application, type of medicine, stability etc.

Currently, there are three important types of dose-dispensing machines on the market, namely a Tosho machine type Main-Topra 2441 CE. This machine doses in small plastic bags and doses up to 244 different compositions. Another type Main-Topra 4001 CE doses up to 400 different compositions with the same speed as Main-Topra 2441 CE (45 bags/min).

Automed Technologies Inc, USA, has e.g. the type ATC 212 on the European market. This machine doses in small plastic bags and doses up to 212 different compositions. The machine packs 25 bags/min. Other recent types are improved with respect to number of different compositions to be packed (330 or 520) and the speed is increased to 60 bags/min.

Hyupshin Medical co. Ltd has a dose-dispensing machine, ATDPS, which doses in small plastic bags and doses up to 352 different compositions. The speed is 60 bags/min. Furthermore, new machines have been developed (ATDPS JV-500SL and ATDPS JV-352SL), which doses up to 500 different compositions with the same speed (60 bags/min).

Due to the different size and shapes of tablets and capsules, the machines are supplied with different types of cassettes and rotary parts, which ensure that only one tablet or capsule is dosed at the same time. The main body of the cassettes is well shielded from light, it is dust-tight and damp-proof, so the cassettes are well-suited to store the medicine. Misplacing the cassettes is not possible because of a safety lock. Tablets and capsules will not be stored in the cassettes for more than a defined period of time to ensure the quality of the compositions. The machines will make a notice when a composition has been stored in the cassettes for more than this period of time. With respect to the size of the tablets, the following requirements should be met in order to ensure that the tablets can be packed with a dose-dispensing machine: The requirements are dynamic and may change over time.

Round tablet

Length/Diameter

Thickness

| Distributor | Interval | Length (mm) | Thickness (mm) |
|---|---|---|---|
| Tosho | Minimum | | |
| | Maximum | 14.0 | 9.4 |
| Hyupshin | Minimum | 5.5 | 1.5 |
| | Maximum | 13.2 | 6.7 |
| Automed Tech. | Minimum | 4.6 | 2.2 |
| | Maximum | 14.0 | 7.0 |

Oval tablet

Length

Thickness

Width

| Distributor | Interval | Length (mm) | Thickness (mm) | Width (mm) |
|---|---|---|---|---|
| Tosho | Minimum | | | |
| | Maximum | 21.5 | 7.5 | 7.5 |
| Hyupshin | Minimum | 8.5 | 2.7 | 4.0 |
| | Maximum | 20.0 | 7.7 | 10.0 |
| Automed Tech. | Minimum | 6.9 | 2.2 | 4.6 |
| | Maximum | 21.0 | 7.5 | 11.7 |

The above-mentioned dimension for a round or an oval tablet may be changed and still fit into the specified dose-dispensing machine. Experiments performed by the present inventors have shown that a variation in a range of ±20% is acceptable, preferable ±10%. With respect to the size, one of the major problems, the inventors were faced with was to reduce the thickness of the tablets. This was solved by using a proper combination of active ingredient(s) and pharmaceutically acceptable excipients and by a careful selection of a suitable particle size and/or crystal form of the calcium-containing compound, the properties of the excipients and the preparation method.

It is of importance that the tablets do not create dust and as mentioned above, the tablets must be sufficiently robust to withstand the mechanical stress employed by using a dose-dispensing machine.

The present inventors have found that it is possible to apply a thin film coating on the tablets in order e.g. to increase the swallowability or in order to minimize any dust problems or problems relating to crushing strength or friability. To this end it should be noted that application of a film coating cannot repair substantial problems with respect to crushing strength or friability, but it can just give the final push in the right direction. Furthermore, only a thin film coating must be applied in order to maintain an acceptable mouthfeel, i.e. the coating may be applied in an amount that corresponds to an increase in weight of the tablet of at the most about 2% w/w such as, e.g., at the most about 1.5% w/w, at the most about 1% w/w or in a range of from about 0.25% to 0.75% w/w based on the weight of the uncoated tablets.

In the following are given dimensions of marketed tablets containing calcium carbonate Dimensions of calcium carbonate containing tablet

| | Length [mm] | Height [mm] | Width [mm] |
|---|---|---|---|
| Calcipos-D swallowable (oval/capsule) | 19.3 | 5.6 | 8.7 |
| Calcipos-D chewing tablet (round) | 17.2 | 7.0 | — |
| Calcichew chewing tablet (round) | 16.1 | 7.0 | — |
| Ideos chewing tablet (quadratic) | 19.6 | 4.8 | 19.6 |

Calcium-Containing Compound

The calcium-containing compound contained in a tablet made according to the invention is a physiologically tolerable calcium-containing compound that is therapeutically and/or prophylactically active.

Calcium is essential for a number of key functions in the body, both as ionized calcium and a calcium complex (Campell A K. Clin Sci 1987; 72:1-10). Cell behaviour and growth are regulated by calcium. In association with troponin, calcium controls muscle contraction and relaxation (Ebashi S. Proc R Soc Lond 1980; 207:259-86).

Calcium selected channels are a universal feature of the cell membrane and the electrical activity of nerve tissue and the discharge of neurosecretory granules are a function of the balance between intracellular and extra cellular calcium levels (Burgoyne R D. Biochim Biophys Acta 1984; 779:201-16). The secretion of hormones and the activity of key enzymes and proteins are dependent on calcium. Finally calcium as a calcium phosphate complex confers rigidity and strength on the skeleton (Boskey A L. Springer, 1988:171-26). Because bone contains over 99% of the total body calcium, skeletal calcium also serves as the major long-term calcium reservoir.

Calcium salts such as, e.g., calcium carbonate is used as a source of calcium especially for patients suffering from or at risk of osteoporosis. Moreover, calcium carbonate is used as an acid-neutralizing agent in antacid tablets.

As mentioned above, calcium has a number of important functions within the mammalian body in particular in humans. Furthermore, in many animal models, chronic low calcium intake produces osteopenia. The osteopenia affects cancellous bone more than cortical bone and may not be completely reversible with calcium supplementation. If the animal is growing reduced calcium intake leads to stunting. In the premature human neonate the higher the calcium intake, the greater the increase in skeletal calcium accretion which, if high enough, can equal gestational calcium retention. During growth chronic calcium deficiency causes rickets. Calcium supplements in both pre- and postpubertal healthy children leads to increased bone mass. In adolescents the higher the calcium intake, the greater the calcium retention, with the highest retention occurring just after menarche. Taken together, these data suggest that in children and adolescents considered to be taking an adequate intake of calcium, peak bone mass can be optimized by supplementing the diet with calcium. The mechanisms involved in optimizing deposition of calcium in the skeleton during growth are unknown.

They are probably innate properties of the mineralization process that ensures optimal calcification of the osteoid if calcium supplies are high. The factors responsible for stunting of growth in states of calcium deficiency are also unknown but clearly involve growth factors regulating skeletal size.

In adults calcium supplementation reduces the rate of age-related bone loss (Dawson-Hughes B. Am J Clin Nut 1991; 54:S274-80). Calcium supplements are important for individuals who cannot or will nor achieve optimal calcium intakes from food. Furthermore, calcium supplement is important in the prevention and treatment of osteoporosis etc.

Furthermore, calcium may have anticancer actions within the colon. Several preliminary studies have shown high calcium diets or intake of calcium supplementation is associated with reduced colon rectal cancer. There is increasing evidence that calcium in combination with acetylsalicylic acid (ASA) and other non-steroidal anti-inflammatory drugs (NSAIDS) reduce the risk of colorectal cancer.

Recent research studies suggest that calcium might relieve premenstrual syndrome (PMS). Some researchers believe that disruptions in calcium regulation are an underlying factor in the development of PMS symptoms. In one study, half the women of a 466 person group of pre-menopausal women from across the U.S. were tracked for three menstrual cycles and were given 1200 mg of calcium supplements daily throughout the cycle. The final results showed that 48% of the women who took placebo had PMS related symptoms. Only 30% of those receiving calcium tablets did.

Calcium salts like e.g. calcium carbonate is used in tablets and due to the high dose of calcium required, such tablets are often in the form of chewable tablets. It is a challenge to formulate e.g. chewable tablets containing a calcium salt, which tablets have a pleasant taste and an acceptable mouth feel without the characteristic dominating taste or feeling of chalk.

A calcium-containing compound for use according to the invention may be e.g. bisglycino calcium, calcium acetate, calcium carbonate, calcium chloride, calcium citrate, calcium citrate malate, calcium cornate, calcium fluoride, calcium glubionate, calcium gluconate, calcium glycerophosphate, calcium hydrogen phosphate, calcium hydroxyapatite, calcium lactate, calcium lactobionate, calcium lactogluconate, calcium phosphate, calcium pidolate, calcium stearate and tricalcium phosphate. Other calcium sources may be water-soluble calcium salts, or complexes like e.g. calcium alginate, calcium-EDTA and the like or organic compounds containing calcium like e.g. calcium organophosphates. Use of bone meal, dolomite and other unrefined calcium sources is discouraged because these sources may contain lead and other toxic contaminants. However, such sources may be relevant if they are purified to a desired degree.

The calcium-containing compound may be used alone or in combination with other calcium-containing compounds.

Of specific interest is bisglycino calcium, calcium acetate, calcium carbonate, calcium chloride, calcium citrate, calcium citrate malate, calcium cornate, calcium fluoride, calcium glubionate, calcium gluconate, calcium glycerophosphate, calcium hydrogen phosphate, calcium hydroxyapatite, calcium lactate, calcium lactobionate, calcium lactogluconate, calcium phosphate, calcium pidolate, calcium stearate and tricalcium phosphate. Mixtures of different calcium-containing compounds may also be used. As appears from the examples herein, calcium carbonate is especially suitable for use as a calcium-containing compound and calcium carbonate has a high content of calcium.

Of particular interest is calcium carbonate.

Normally, a tablet made according to the invention contains an amount of the calcium-containing compound corresponding to from about 100 to about 1000 mg Ca such as, e.g., from about 150 to about 800 mg, from about 200 to about 700 mg, from about 200 to about 600 mg or from about 200 to about 500 mg Ca.

Calcium Carbonate

Calcium carbonate can be in three different crystal structures: calcite, aragonite and vaterite. Mineralogically, these are specific mineral phases, which relate to the distinct arrangement of the calcium, carbon and oxygen atoms in the crystal structure. These distinct phases influence the shape and symmetry of the crystal forms. For example, calcite is available in four different shapes: scalenohedral, prismatic, spherical and rhombohedral, and aragonit crystals can be obtained as e.g. discrete or clustered needle-like shapes. Other shapes are also available such as, e.g., cubic shapes (Scoralite 1A+B from Scora).

As shown in the examples herein, a particular suitable quality of calcium carbonate is calcium carbonate having a mean particle size of 60 μm or less such as, e.g., 50 μm or less or 40 μm or less.

Furthermore, an interesting quality of calcium carbonate has a bulk density below 2 g/mL.

Calcium carbonate 2064 Merck (available from Merck, Darmstadt, Germany) that has a mean particle size of 10-30 μm, an apparent bulk density of 0.4 to 0.7 g/mL, and a specific surface area of 0.3 $m^2/g$;

Calcium carbonate 2069 Merck (available from Merck, Darmstadt, Germany) that has a mean particle size of approx. 3.9 μm, and an apparent bulk density of 0.4 to 0.7 g/mL;

Scoralite 1A (available from Scora Watrigant SA, France) has a mean particle size of 5 to 20 μm, an apparent bulk density of 0.7 to 1.0 g/mL, and a specific surface area of 0.6 $m^2/g$;

Scoralite 1 B (available from Scora Watrigant SA, France) has a mean particle size of 10-25 μm, an apparent bulk density of 0.9 to 1.2 g/mL, and a specific surface area of 0.4 to 0.6 $m^2/g$;

Scoralite 1A+B (available from Scora Watrigant SA, France) have a mean particle size of 7-25 μm, an apparent bulk density of 0.7 to 1.2 g/mL, and a specific surface area of 0.35 to 0.8 $m^2/g$;

Pharmacarb LL (available from Chr. Hansen, Mahawah New Jersie) L has a mean particle size of 12-16 μm, an apparent bulk density of 1.0 to 1.5 g/mL, and a specific surface area of 0.7 $m^2/g$;

Sturcal H, Sturcal F and Sturcal M (available from Specialty Minerals, Bethlehem, Pa.); Sturcal L has a mean particle size of approx. 7 μm, an apparent bulk density of 0.78 to 0.96 g/mL, Sturcal L consists of scalenohedral shaped crystals;

Sturcal H has a mean particle size of approx. 4 μm, an apparent bulk density of 0.48 to 0.61 g/mL;

Sturcal F has a mean particle size of approx. 2.5 μm, an apparent bulk density of 0.32 to 0.43 g/mL;

Sturcal M has a mean particle size of 7 μm, an apparent bulk density of 0.7 to 1.0 g/mL, and a specific surface area of 1.0 $m^2/g$;

Mikhart 10, SPL, 15, 40 and 65 (available from Provencale, Provencale, France);

Mikhart 10 has a mean particle size of 10 μm,

Mikhart SPL has a mean particle size of 20 μm,

Mikhart 15 has a mean particle size of 17 μm,

Mikhart 40 has a mean particle size of 30 μm, an apparent bulk density of 1.1 to 1.5 g/mL;

Mikhart 65 has a mean particle size of 60 μm, an apparent bulk density of 1.25 to 1.7 g/mL;

Omyapure 35, (available from Omya S.A.S, Paris, France) has a mean particle size of 5-30 μm, and a specific surface area of 2.9 m$^2$/g;

Socal P2PHV (available from Solvay, Brussels, Belgium) has a mean particle size of 1.5 μm, an apparent bulk density of 0.28 g/mL, and a specific surface area of 7.0 m$^2$/g;

Calci Pure 250 Heavy, Calci Pure 250 Extra Heavy and Calci Pure GCC HD 212 with a mean particle size of 10-30 μm, an apparent bulk density of 0.9-1.2 g/ml, and a specific surface area of 0.7 m$^2$/g (available from Particle Dynamic Inc., St. Louis Mont.).

The content of the calcium-containing compound in a tablet made according to the present invention is in a range from about 40% to about 100% w/w such as, e.g., from about 45% to about 98% w/w, from about 50% to about 95% w/w, from about 55% to about 90% w/w or at least about 60% w/w, at least about 65% w/w, at least about 70% w/w or at least about 75% w/w.

Normally, the dose of calcium for therapeutic or prophylactic purposes is from about 350 mg (e.g. newborn) to about 1200 mg (lactating women) daily. The amount of the calcium-containing compound in the tablets can be adjusted to that the tablets are suitable for administration 1-4 times daily, preferably once or twice daily.

As mentioned above, the granulate obtained by the method according to the invention may be used as such, but it is also very suitable for further manufacturing into solid dosage forms like e.g. tablets, capsules or sachets.

In the examples herein guidance is given of which parameters that are important to take into account and how to select a suitable set-up in order to prepare chewable tablets or swallowable tablets, respectively. Based on this guidance a person skilled in the art will know how to adjust the composition and the various process parameters in order to obtain a desired calcium-containing product.

When manufacturing tablets it is often necessary to add one or more pharmaceutically acceptable excipients (e.g. lubricants) in order to avoid adherence and/or increase flowability of the granulate obtained. Accordingly, the method may also comprise a step of mixing the granulate obtained with one or more pharmaceutically acceptable excipients.

In the event that it is desired to include other active substances than the calcium-containing compound, the method may also comprise a step of adding one or more therapeutically, prophylactically and/or diagnostically active substance to the granulate obtained.

Such substances include one or more nutrients such as, e.g., one or more vitamins or minerals. In a specific embodiment, the further active substance is a D-vitamin such as, e.g., $D_3$ vitamin, $D_2$ vitamin or derivatives thereof.

D Vitamin or Other Active Substances

A granulate or tablet made according to the invention may comprise a further therapeutically and/or prophylactically active substance, or it may contain one or more nutrients such as, e.g. one or more vitamins or minerals. Of specific interest are e.g. vitamin B, vitamin C, vitamin D and/or vitamin K and minerals like e.g. zinc, magnesium, selenium etc.

Of particular interest are one or more D-vitamin compounds such as, e.g., Vitamin $D_2$ (ergocalciferol) and Vitamin $D_3$ (cholecalciferol) including dry vitamin $D_3$, 100 CWS available from Roche and dry vitamin $D_3$ 100 GFP available from BASF.

In addition to its action on calcium and skeletal homeostasis, vitamin D is involved in the regulation of several major systems in the body. The actions of vitamin D are medicated at the genome by a complex formed by 1,25-(OH)$_2$ vitamin D mainly produced in the kidney, with the vitamin D receptor (VDR). The latter is widely distributed in many cell types. The 1,25-(OH)$_2$ vitamin DNDR complex has important regulatory roles in cell differentiation and in the immune system. Some of these actions are probably dependant on the ability of certain tissues other than the kidney to produce 1,25-(OH)$_2$ vitamin D locally and act as a paracrine (Adams J S et al. Endocrinology 1996; 137:4514-7).

In humans, deficiency of vitamin D results in rickets in children and osteomalacia in adults. The basic abnormality is a delay in the rate of mineralization off osteoid as it is laid down by the osteoblast (Peacock M. London Livingstone, 1993:83-118). It is not clear whether this delay is due to a failure of a 1,25-(OH)$_2$ vitamin D-dependant mechanism in the osteoblast or to reduced supplies of calcium and phosphate secondary to malabsorption or a combination of both. Accompanying the mineralization delay, there is reduced supply of calcium and phosphate, severe secondary hyperparathyroidism with hypocalcaemia and hypophosphatemia and increased bone turnover.

Vitamin D insufficiency, the preclinical phase of vitamin D deficiency, also causes a reduced calcium supply and secondary hyperparathyroidism, albeit of a milder degree than found with deficiency. If this state remains chronic, osteopenia results. The biochemical process underlying this state of calcium insufficiency is probably inappropriate level of 1,25-(OH)$_2$ vitamin D due to a reduction in its substrate 25-OHD (Francis R M et al. Eur J Clin Invest 1983; 13:391-6). The state of vitamin D insufficiency is most commonly found in the elderly. With age there is a decrease in serum 25-OH vitamin D due to decreased sunlight exposure and possible to decreased skin synthesis. Furthermore, in the elderly the condition is exacerbated by a decrease in calcium intake and a paradoxical decrease in calcium absorption. The reduction in renal function with age giving rise to reduced renal 1,25-(OH)$_2$ vitamin D production may be a contributing factor. There are a number of studies of the effects of vitamin D supplementation on bone loss in the elderly. Some are without calcium supplementation and others are with calcium supplementation. It appears from the studies that although vitamin D supplementation is necessary to reverse deficiency and insufficiency, it is even more important as far as the skeleton is concerned to provide calcium supplementation since the major skeletal defect is calcium deficiency. In literature based on clinical trials, recent findings suggest trends of need for higher doses of vitamin D for the elderly patients (Compston J E. BMJ 1998; 317:1466-67). An open quasi-randomised study of annual injections of 150.000-300.000 IU of vitamin D (corresponding to approx. 400-800 IU/day) showed a significant reduction in overall fracture rate but not in the rate of hip fracture in treated patients (Heikinheimo R J et al. Calcif Tissue Int 1992; 51:105-110).

As it appears from above, a combination of calcium and vitamin D is of interest. The recommended Daily Allowance (RDA) of calcium and vitamin $D_3$ are as follows (European Commission. Report on osteoporosis in the European Community. Action for prevention. Office for official Publications of the European Communities, Luxembourg 1998):

| Group | Age (years) | Calcium (mg)* | Vitamin $D_3$ (µg) |
|---|---|---|---|
| Newborn | 0-0.5 | 400 | 10-25 |
| | 0.5-1.0 | 360-400 | 10-25 |
| Children | 1.0-3.0 | 400-600 | 10 |
| | 4.0-7.0 | 450-600 | 0-10 |
| | 8.0-10 | 550-700 | 0-10 |
| Men | 11-17 | 900-1000 | 0-10 |
| | 18-24 | 900-1000 | 0-15 |
| | 25-65 | 700-800 | 0-10 |
| | 65+ | 700-800 | 10 |
| Women | 11-17 | 900-1000 | 0-15 |
| | 18-24 | 900-1000 | 0-10 |
| | 25-50 | 700-800 | 0-10 |
| | 51-65 | 800 | 0-10 |
| | 65+ | 700-800 | 10 |
| Pregnant | | 700-900 | 10 |
| Lactating | | 1200 | 10 |

*RDA of calcium varies from country to country and is being re-evaluated in many countries.

Vitamin D is very sensitive towards humidity and is subject to degradation. Therefore, vitamin D is often administered in a protective matrix. Accordingly, when tablets are prepared containing a vitamin D it is of utmost importance that the compression forces applied during the tabletting step do not decrease the protective effect of the matrix and thereby impair the stability of vitamin D. To this end, the combination of the various ingredients in a granulate or tablet made according to the invention has proved to be very suitable in those cases where vitamin D also is incorporated into the composition as it is possible to employ a relatively low compression force during tabletting and still achieve a tablet with suitable mechanical strength (crushing strength, friability etc.).

Accordingly, the compression step is performed at a compression force that is adjusted with respect to the diameter and the desired height of the tablet so that the compression force applied is at the most 50 kN, at the most about 40 kN, at the most about 30 kN or at the most about 25 kN such as at the most about 20 kN, when tablets having an oval shape of about 19 mm length and about 9.4 mm width and a resulting height of about 5.5-8 mm are obtained. A person skilled in the art will know how to determine a suitable compression force if tablets are prepared with dimensions that deviate from the above.

As indicated above, a tablet containing vitamin D is contemplated to fulfil the following requirements with respect to stability:

After storage in an open petri dish at 25° C. and 60% relative humidity (RH) for 1 week or more such as, e.g., for 2 weeks or more, for 3 weeks or more, for 4 weeks or more, for 1 month or more, for 2 months or more, or for 3 months or more, the content of D vitamin in the tablet should at the most change 20% w/w such as, e.g. at the most about 15% w/w, at the most about 10% w/w or at the most about 5% w/w during the storage period.

After storage e.g. in a closed container at 25° C. and 60% RH the tablet it is stable with respect to the content of D vitamin for 6 months or more such as, e.g. for 8 months or more, for 10 months or more, for 1 year or more, for 1.5 years or more or for 2 years or more and/or it is stable towards storage in a closed container at 30° C. and 65% RH for 2 months or more such as, e.g., for 4 months or more, for 6 months or more, for 1 year or more and/or it is stable towards storage in a closed container at 40° C. and 75% RH for 1 month or more such as, e.g., for 2 months or more or for 3 months or more, i.e the content of D vitamin in the tablet changes at the most 20% w/w such as, e.g. at the most about 15% w/w, at the most about 10% w/w or at the most about 5% w/w during the storage period.

In a specific embodiment at least 50% w/w such as, e.g., at least 60% w/w at least about 70% w/w, at least about 75% w/w or at least about 80% w/w of the D vitamin is released within at the most about 2 hours such as, e.g., at the most about 1.5 hour, at the most about 1 hour, at the most about 45 min or at the most about 30 min. Furthermore, the dissolution time—measured as the time for 60% w/w of the D vitamin of the tablet to be released in a dissolution test according to USP—changes at the most 50% such as, e.g., at the most about 40%, at the most about 30%, at the most about 20%, at the most about 15%, at the most about 10% or at the most about 5% during a time period that starts after 5 days of storage and runs during the remaining storage period.

In a specific embodiment, the invention provides a tablet comprising
i) a calcium-containing compound as an active substance,
ii) a vitamin D, and
iii) optionally one or more pharmaceutically acceptable excipients or actives.

More specifically, the tablet may comprise
i) at least 200 mg of the calcium-containing compound (normal range 200-1500 mg),
ii) at least 5 µg of vitamin D (normal range 5-100 µg–1 µg=40 IU), and
iii) optionally one or more pharmaceutically acceptable excipients or actives.

In a specific embodiment, the invention provides a tablet comprising
i) from about 50% to about 90% w/w of the calcium-containing compound,
ii) from about 0.00029% o about 0.0122% w/w of a vitamin D, and
iii) optionally one or more pharmaceutically acceptable excipients or actives.
with the proviso that the total amount of ingredients corresponds to about 100% w/w.

In particular, the tablet may comprise
i) from about 50% to about 90% w/w of the calcium-containing compound,
ii) from about 5 to about 40% w/w of a sweetening agent,
iii) from about 0.12% to about 4.9% w/w of a vitamin D including a protective matrix,
iv) optionally one or more pharmaceutically acceptable excipients or actives.
with the proviso that the total amount of ingredients corresponds to about 100% w/w.

Figure 4:

In a specific embodiment the tablets have a shape and dimensions essentially as shown in FIG. 4 herein. This shape is especially designed to easily break the tablet into two halves of essentially the same size, i.e. essentially containing the same amount of calcium. The breakage is provided by placing the tablet on a flat surface e.g. a table and then by use of e.g. two fingers pressing simultaneously on each end of the tablet. Due to the fact that the tablet is in contact with the table only in one point this is possible.

Preparation of a Tablet According to the Invention

In general, a tablet according to the invention can be prepared by any suitable process known to a person skilled in the art. The process may include wet granulation e.g. in a high shear mixer or in a fluid-bed apparatus or dry granulation e.g. roller compaction and then compressing the obtained powder into tablets or it may be a direct compression process without any granulation. A person skilled in the art will know how to employ the different techniques optionally with guidance from Remington's Pharmaceutical Sciences, 28 Ed.

Pharmaceutically Acceptable Excipients

In the present context, the term "pharmaceutically acceptable excipient" is intended to denote any material, which is inert in the sense that it substantially does not have any therapeutic and/or prophylactic effect per se. A pharmaceutically acceptable excipient may be added to the active drug substance with the purpose of making it possible to obtain a pharmaceutical composition, which has acceptable technical properties.

The calcium-containing compound is normally admixed with one or more pharmaceutically acceptable excipients before compression into tablets. Such excipients include those normally used in formulation of solid dosage forms such as, e.g. fillers, binders, disintegrants, lubricants, flavouring agents, colouring agents, including sweeteners, pH adjusting agents, buffering agents, stabilizing agents, etc. In the following are given examples of excipients suitable for use in a tablet according to the present invention.

| Excipient | Concentration [% of formulation] |
| --- | --- |
| Sweetening agents | 5-30, if present |
| Artificial sweeteners | 0.05-0.3, if present |
| Flavours | 0.1-3, if present |
| Disintegrating agents | 0.5-5, if present |
| Glidant and lubricants | 0.1-5, if present |
| Fillers/diluents/binders | 0.1-15, if present |
| Film forming agents | 0.1-5, if present |
| Film additives | 0.05-5, if present |

Sweetening Agents:

Examples of suitable sweeteners include dextrose, erythritol, fructose, glycerin, glucose, inositol, isomalt, lactitol, lactose, maltitol, maltose, mannitol, sorbitol, sucrose, tagatose, trehalose, xylitol, etc. Sorbitols e.g. Neosorb PLOOT, Sorbidex P166B0 and Sorbogem Fines Crystalline Sorbitol available from Roquette Freres, Cerestar and SPI Polyols Inc. respectively. Maltisorb P90 (maltitol) available from Roquette Freres, Xylitol CM50, Fructofin CM (fructose) and Lactitol CM50 available from Danisco Sweeteners, Isomalt ST-PF, Gaio Tagatose and Manitol available from Palatinit, Arla Foods and Roquette, Freres respectively. Sorbitol has a sweetening effect (compared to sucrose) of 0.55; maltitol that has a sweetening effect of ≤1; xylitol that has a sweetening effect of 1, isomalt that has a sweetening effect of <0.5, etc. The sweetening effect may be of value in connection with choosing the individual sweetening agents. Thus, if a decreased tablet weight and volume are desired, it is suitable to choose a sweetening agent having a high sweetening effect.

Artificial Sweeteners

Acesulfam potassium, alitame, aspartame, cyclamic acid, cyclamate salt (e.g. calcium cyclamate, sodium cyclamate), neohesperidine dihydrochalcone, neohesperidine hydrochloride, saccharin, saccharin salt (e.g. ammonium saccharin, calcium saccharin, potassium saccharin, sodium saccharin), sucralose, taumatin and mixtures thereof.

Flavours

Aprocot, Lemon, Lemon/Lime, Lime, Orange, Mandarine, such as Aprocot 501.110 AP0551, Lemon 501.051 TP0551, Lemon 501.162 AP0551, Lemon/Lime 501.053 TP0551, Lime 501.054 TP0551, Orange 501.071 AP0551, Orange TP0551, Orange 501.434 P0551, Mandarine 501.AP0551, Lemon Durarome 501.282 TDI1091 available from Firmenich, Kerpen, Germany or Juicy Lemon Flavouring T3602 available from TasteTech, Bristol, England or Lemon Lime Flavour Permseal 11029-31, Lemon Flavour Permseal 12028-31, Lemon Flavour Ultradseal 96918-71 Available from Givaudan Schweiz AG, Kemptthal, Schweiz or Lemon Flavour Powder 605786, Lemon Flavour Powder 605897 available from Frey+Lau Gmbh, Henstedt-Ulzburg, Germany Disintegrating Agents Alginic acid—alginates, carboxymethylcellulose calcium, carboxymethylcellulose sodium, crospovidone, hydroxypropylcellulose, hydroxypropylmethylcellulose (HPMC), cellulose derivatives such as low-substituted hydroxypropylcellulose (e.g LH 11, LH 20, LH 21, LH 22, LH 30, LH 31, LH 32 available from Shin-Etsu Chemical Co.) and microcrystalline cellulose, polacrilin potassium or sodium, polyacrylic acid, polycarbofil, polyethylene glycol, polyvinylacetate, polyvinylpyrrolidone (e.g. Polyvidon® CL, Poly-vidon® CL-M, Kollidon® CL, Polyplasdone® XL, Polyplasdone® XL-10); sodium carboxymethyl starch (e.g. Primogel® and Explotab®), sodium croscarmellose (i.e. cross-linked carboxymethylcellulose sodium salt; e.g. Ac-Di-Sol®), sodium starch glycolate, starches (e.g potato starch, maize starch, rice starch), pre-gelatinised starch.

Those skilled in the art will appreciate that it is desirable for compressible tablets to disintegrate within 30 minutes, more desirable within 15 min, most desirable within 5 min; therefore, the disintegrant used preferably results in the disintegration of the tablet within 30 minutes, more preferable within 15 min, most preferable within 5 min.

Effervescent agent (e.g. mixture of sodium hydrogen carbonate (carbonates, alkaline, alkaline earth metals) and citric acid (tartaric acid, fumaric acid etc.)).

Glidants and Lubricants

Glidants and lubricants may be incorporated such as stearic acid, metallic stearates, talc, waxes and glycerides with high melting temperatures, hydrogenated vegetabable oils, colloidal silica, sodium stearyl fumarate, polyethylenglycols and alkyl sulphates.

Suitable lubricants include talc, magnesium stearate, calcium stearate, stearic acid, hydrogenated vegetable oils and the like. Preferably, magnesium stearate is used.

Fillers/Diluents/Binders

Dextrins, maltodextrins (e.g. Lodex® 5 and Lodex® 10), dextrose, fructose, glucose, inositol, erythritol, isomalt, lactitol, lactose (e.g., spray-dried lactose, α-lactose, β-lactose, Tabletose®, various grades of Pharmatose®, Microtose or Fast-Floc®), maltitol, maltose, mannitol, sorbitol, sucrose, tagatose, trehalose, xylitol, low-substituted hydroxypropylcellulose (e.g LH 11, LH 20, LH 21, LH 22, LH 30, LH 31, LH 32 available from Shin-Etsu Chemical Co.), microcrystalline cellulose (e.g., various grades of Avicel®, such as Avicel® PH101, Avicel® PH102 or Avicel® PH105, Elcema® P100, Emcocel®, Vivacel®, Ming Tai® and Solka-Floc®), starches or modified starches (e.g potato starch, maize starch, rice starch, pre-gelatinised starch), polyvinylpyrrolidone, polyvinylpyrrolidone/vinyl acetate copolymer, agar (e.g. sodium alginate), calcium hydrogen phosphate, calcium phosphate (e.g. basic calcium phosphate, calcium hydrogen phosphate), calcium sulphate, carboxyalkylcellulose, dextrates, dibasic calcium phosphate, gelatine, gummi arabicum, hydroxypropyl cellulose, hydroxypropylmethylcellulose, magnesium carbonate, magnesium chloride, methylcellulose, polyethylene glycol, polyethylene oxide, polysaccharides e.g. dextran, soy polysaccharide, sodium carbonate, sodium chloride, sodium phosphate.

Surfactants/Enhancers

Surfactants may be employed such as

Non-ionic (e.g., polysorbate 20, polysorbate 21, polysorbate 40, polysorbate 60, polysorbate 61, polysorbate 65, polysorbate 80, polysorbate 81, polysorbate 85, polysorbate 120, sorbitan monoisostearate, sorbitan monolaurate, sorbitan monopalmitate, sorbitan monostearate, sorbitan monooleate, sorbitan sesquioleate, sorbitan trioleate, glyceryl monooleate and polyvinylalkohol),
anionic (e.g., docusate sodium and sodium lauryl sulphate) cationic (e.g., benzalkonium chloride, benzethonium chloride and cetrimide)

Fatty acids, fatty alcohols and fatty esters, for example:
ethyl oleate, sodium oleate, lauric acid, methyl laurate, oleic acid, sodium caprate
Dioctyl calcium sulfosuccinate, dioctyl potassium sulfosuccinate, dodecyltrimethylammonium bromide, hexadecyltrimethylammonium bromide, trimethyltetradecylammonium bromide, polyoxyethylene ethers (polyoxyethylene-9-lauryl ether), sodium dodecyl sulphate, sodium dioctyl sulfosuccinate, sodium laurate, sodium 5-methoxysalicylate, sodium salicylate;

bile salts, for example:
sodium deoxycholate, deoxycholic acid, sodium cholate, cholic acid, sodium glycocholate, sodium glycodeoxycholate, sodium taurocholate, sodium taurodeoxycholate;

cytoadhesives, for example:
lectins (e.g. *Lycopersicon Esculentum* Agglutinin, Wheat Germ Agglutinin, *Urtica Dioica* Agglutinin).
N-acylated amino acids (especially N-[8-(2-hydroxy-4-methoxy)benzoyl]amino caprylic acid (4-MOAC), 4-[4-(2-hydroxybenzoyl)amino]butyric acid, sodium N-[8-(2-hydroxybenzoyl)amino]-caprylate);

phospholipids, for example:
hexadecylphosphocholine, dimyristoylphosphatidylglycerol, lysophosphatidylglycerol, phosphatidylinositol, 1,2-di (2,4-octadecadienoyl)-sn-glycerol-3-phosphorylcholine and phosphatidylcholines (e.g. didecanoyl-L-phosphatidylcholine, dilauroylphosphatidylcholine, dipalmitoylphosphatidylcholine, distearoylphosphatidylcholine), lysophosphatidylcholine is of particular interest;

cyclodextrins, for example:
β-cyclodextrin, dimethyl-β-cyclodextrin, γ-cyclodextrin, hydroxypropyl β-cyclodextrin, methyl cyclodextrin; especially dimethyl-β-cyclodextrin is of particular interest;

fusidic acid derivatives, for example:
sodium taurodihydrofusidate, sodium glycodihydrofusidate, sodium phosphate-dihydrofusidate; especially sodium taurodihydrofusidate is of particulare interest;

others:
sodium salts of e.g. glycyrrhizic acid, capric acid, alkanes (e.g. azacycloalkanes), amines and amides (e.g. N-methylpyrrolidone, Azone), amino acids and modified amino acids compounds (e.g. acetyl-L-cysteine), polyols (e.g. propyleneglycol, hydrogels), sulfoxides (e.g. dimethylsulfoxide), terpenes (e.g. carvone), ammonium glycyrrizinate, hyluronic acid, isopropyl myristate, n-lauryl-beta-D-maltopyranoside, saponins, DL-octanonylcarnitine chloride, palmitoyl-DL-carnitine chloride, DL-stearoylcarnitine chloride, acylcarnitines, ethylenediaminedihydro-chloride, phosphate-dihydrofusidate, sodium CAP); especially n-lauryl-beta-D-maltopyranoside is of particular interest, alpha 1000 peptide, peptide MW<1000 comprising at least 6 mol % of aspartatic- and glutamic Acid, decomposed royal jelly, prebiotica, butyrate, butyric acid, vitamin $D_2$, vitamin $D_3$, hydroxy-vitamin $D_3$, 1.25-dihydroxy-vitamin $D_3$, spirulina, proteoglycan, soyahydrolysate, lysin, lactic acid, di-fructose-anhydrid, vylitol Ca-(lactate), hydrolyzate of casein in particular a caseinoglycomacropeptide, negative ionization of $CaCO_3$, acetylsalicylic acid, vitamin K, creatin.

Film Forming Agents:
Hydrofilic film formers such as hydroxypropylmethylcellulose (HPMC) (e.g. HPMC E5, HPMC E15), hydroxyethylcellulose, hydroxypropylcellulose, polydextrose and maltodextrin, Sepifilm™ and Sepifilm™ LP available from Seppic S.A., Pharmacoat® available from Shin-Etsu Chemical Co.

Film Additives
Acetylated monoglyceride, acetyltributyl, acetyltributyl citrate, acetyltriethyl citrate, benzyl benzoate, calcium stearate, castor oil, cetanol, chlorebutanol, colloidal silica dioxide, dibutyl phthalate, dibutyl sebacate, diethyl oxalate, diethyl malate, diethyl maleate, diethyl malonate, diethyl fumarate, diethyl phthalate, diethyl sebacate, diethyl succinate, dimethylphthalate, dioctyl phthalate, glycerin, glyceroltributyrate, glyceroltriacetate, glyceryl behanate, glyceryl monostearate, hydrogenated vegetable oil, lecithin, leucine, magnesium silicate, magnesium stearate, polyethylene glycol, propylene, glycol, polysorbate, silicone, stearic acid, talc, titanium dioxide, triacetin, tributyl citrate, triethyl citrate, zinc stearate, wax.

The invention is further illustrated in the following non-limiting examples.

LEGENDS TO FIGURES

Figure 2:
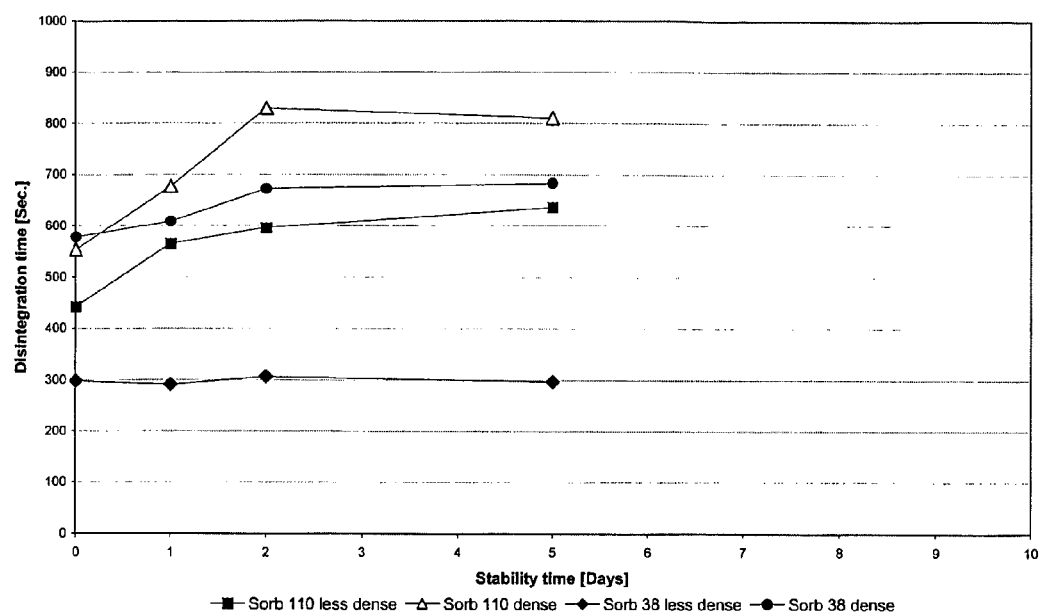
Figure 3:
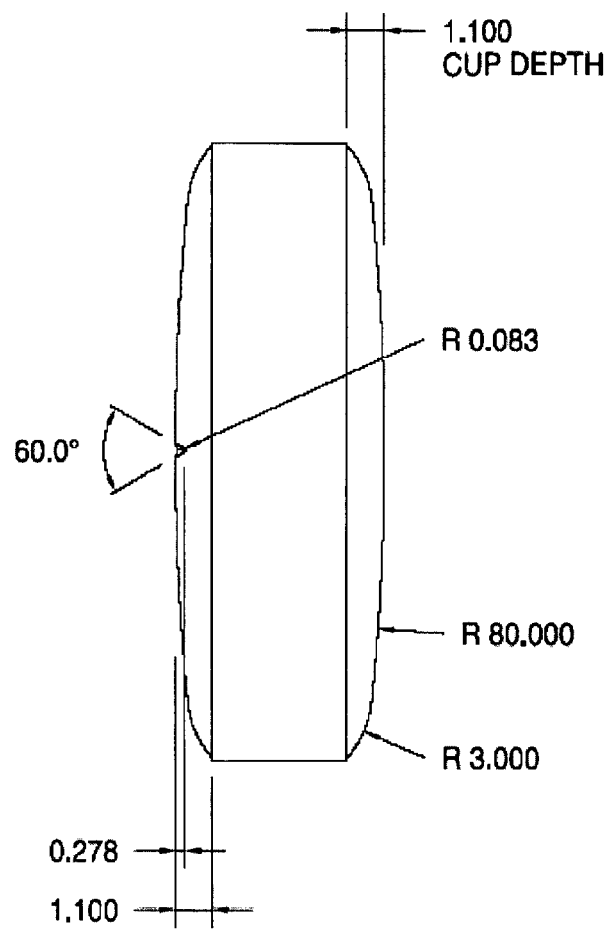

FIG. 1 shows crushing strength stability of tablets based on wet granulation.
FIG. 2 shows disintegration stability of tablets based on wet granulation.
FIG. 3 shows a tablet design.
FIG. 4 shows how to divide a tablet according to the design of FIG. 3.

METHODS

Sensory test: ISO-6564, Sensory analysis—Methodology—Flavour profile methods
ISO-5495 Sensory Analysis—Methodology—Paired comparison test
ISO 8589 Sensory analysis—General guidance for the design of test rooms
ISO 8586 1 Sensory analysis—General guidance for the selection, training and monitoring of assessors
Crushing strength: According to Ph.Eur. 2.9.8
Friability: According to Ph.Eur. 2.9.7
Disintegration time According to Ph.Eur. 2.9.1
Dissolution: According to Ph.Eur. 2.9.3

EXAMPLES

In the examples below, the following materials have been employed:

| | | |
|---|---|---|
| Scoralite 1 B mainstream | Scora Watrigant S.A., France | Calcium carbonate |
| Maltisorb P 90 | Roquette Freres, Estrem, France | Maltitol |
| Xylitol CM 50 | Danisco Sweeteners, Kotka, Finland | Xylitol |

-continued

| | | |
|---|---|---|
| Kollidon 90 | BASF AG, Ludwigshafen, Germany | Polyvinylpyrrolidone 90 (PVP 90) |
| Starch 1500 | Colorcon, Kent, England | Partially pre-gelatinised maize starch |
| Sweetmaster Ace, Acesulfam K | Brøste A/S, Lyngby, Denmark | Acesulfam potassium |
| Magnesium stearate | Peter Greven Netherland C.V | Magnesium stearate |
| Vitamin $D_3$ | Roche, Sisseln, Swiss | Vitamin $D_3$ (colecalciferol) 100.000 IU/g |
| Sorbidex P 166BO | Cerestar, Mechelen, Belgium | Sorbitol 38 μm |
| Neosorb P100T | Roquette Freres, Estrem, France | Sorbitol 100 μm |
| Microcrystaline Cellulose PH 101 | Ming-Tai Chemical Co., Taiwan | Cellulose Microcrystalline |
| Aspartame | Ajinomoto | Aspartame |
| Hypromellose E15 | Dow Chemical Co., Midland, Michigan | Hydroxypropyl methylcellulose (HPMC 2910, USP XXI Suppl2) |
| Talc | Luzenac, Italy | Talc |
| Propylene glucol | Lyondell Chemie, France | Propylene glucol |
| Sepifilm LP 010 | Seppic S.A., Paris, France | A powder mixture, only water needs to be added to obtain a ready to use film |

EXAMPLES

Example 1

Impact of Different Production Methods on the Size of Calcium Carbonate Tablets

This experiment was carried out in large production with a batch size of approx. 40.000 tablets. The experiment was performed in order to investigate whether the technique used for manufacturing granulate for the product had any impact on tablet dimensions especially the tablet height.

The techniques in question were:
i) Wet massing in high shear mixer,
ii) Fluid bed granulation, and
iii) Roller compaction.

TABLE 1

| | | Composition | | | | |
|---|---|---|---|---|---|---|
| | | High shear mixer | | | Fluid | |
| | Raw material | Batch 1 per 1000 tabl. [g] | Batch 2 per 1000 tabl. [g] | Batch 3 per 1000 tabl. [g] | bed Batch 4 per 1000 tabl. [g] | Roller compaction Batch 5 per 1000 tabl. [g] |
| I | Scoralite 1B Mainstream | 1250.0 | 1250.0 | 1250.0 | 1250.0 | 1250.0 |
| III | Vitamin D3 | — | — | 4.4 | — | — |
| IV | Maltisorb P90 | 45.0 | 120.0 | 45.0 | — | — |
| V | Xylitol CM 50 | 195.0 | 120.0 | 195.0 | — | — |
| VI | Sorbidex P 166B0 | — | — | — | — | 385.5 |
| VII | Neosorb P100T | — | — | — | 390.0 | — |
| VIII | Polyvinylpyrrolidone 90 | 6.0 | 5.0 | 6.0 | 36.4 | — |
| IX | Starch 1500 | 54.0 | 54.0 | 54.0 | — | — |
| X | Microcrystalline cellulose PH 101 | — | — | — | — | 75.0 |
| XI | Acesulfam K | 1.0 | 1.0 | 1.0 | — | 1.0 |
| XII | Aspartame | — | — | — | 1.0 | — |
| XIII | Flavour Lemon Powder | 7.0 | 7.0 | 7.0 | — | 7.5 |
| XIV | Lemon flavour granulate | — | — | — | 50.68 | — |
| XV | Magnesium stearate | 6.5 | 6.5 | 6.5 | 6.0 | 6.0 |
| XVI | Purified water | 65.5 | 65.5 | 65.5 | 73.0 | — |
| | Tablet weight | 1565.0 | 1564.0 | 1569.0 | 1734.08 | 1725.0 |

Manufacture of Batch 1-3:

The granulating fluid is manufactured by dissolving VIII in X.

IV and V are passed through a suitable screen and mixed together with I in a 220 l high shear mixer for 1 min at impeller speed 110 rpm and chopper speed 1500 rpm. The powder mass is wetted with the granulation fluid at impeller speed 110 rpm and chopper speed 1500 rpm. Wet massing is continued for 5 min at impeller speed 220 rpm and chopper speed 1500 rpm. The wet massed powder is dried in a fluid bed until the absolute water content is below 0.5%.

The rest of the excipients are admixed to the dried granulate.

Manufacture of Batch 4:

The granulating fluid is manufactured by dissolving VIII in XVI.

VII is passed through a suitable screen and mixed with I in a Glatt fluid bed granulator. The powder mixture is granulated by spraying the granulating fluid on the powder bed, while the fluidizing process is ongoing.

The remaining parts of the excipients XII, XIV and XV are admixed to granulate.

Manufacture of Batch 5

IV and V or VI are passed through a suitable screen and mixed together with I or II in a 220 l high shear mixer for 1 min at impeller speed 110 rpm and chopper speed 1500 rpm.

The powder mixture is granulated using a roller compactor (Gerteis 3W-Polygran)

The roller compaction was based on a setup with knurled rollers and control. The key set up parameters are: Gap Width (GW), Force (F), Roller Speed (RS) and screen size.

| Roller compaction conditions | |
| --- | --- |
| GW, mm | 3.5 |
| F, kN/cm | 12 |
| RS, rpm | 10 |
| Screen size, mm | 1.5 | followed by admixing of the remaining excipients X, XI, XIII and XV.

For all the granulates from batch 1-5 tablets are compressed using a Fette 1090 and capsule shaped punch design (9.4×18.9 mm)

TABLE 2

Adjusted tablet height for batch 1-5.

| | Compression force [kN] | Adjusted Tablet height (tablet height/tablet weight) [mm/mg] * 10³ | Tablet length [mm] |
| --- | --- | --- | --- |
| Batch 1 | 22.0 | 3.96 | 19.13 |
| Batch 2 | 20.0 | 3.98 | 19.11 |
| Batch 3 | 20.1 | 4.03 | 19.13 |
| Batch 4 | 19.9 | 4.30 | 19.04 |
| Batch 5 | 20.9 | 4.11 | 19.07 |

The results shows that the lowest tablet height is obtained by wet massing in high shear mixer (batch 1-3), a larger tablet height is obtained by roller compaction (batch 5) and the highest tablet is achieved by fluid bed granulation (batch 4).

Example 2

Tablets with Different Coating Materials

Dispensed in Dose Dispensing Machines

The objective of this experiment was to test tablets with different coatings in dose dispensing machines.

Tablets manufactured according to batch 1, 2 and 3 in Example 5 were produced. The tablets were coated with a hydroxypropylmethyl cellulose film or a Sepifilm LP 010 using a lab-size Combi-Coata (Niro) (top spray).

TABLE 3

Type of film applied.

| | Hydroxypropylmethyl cellulose film 0.75% weight gain | Sepi-film 5% weight gain |
| --- | --- | --- |
| Batch 1 | X | |
| Batch 2 | X | |
| Batch 3 | | X |

Composition of hydroxypropylmethyl cellulose film

| | Raw materials | % (w/w) |
| --- | --- | --- |
| I | Hypromellose E15 | 2.5 |
| II | Talc | 1.5 |
| III | Propylene glycol | 0.5 |
| IV | Purified water | 95.5 |

Composition of Sepifilm LP 010

| | Raw materials | % w/w |
| --- | --- | --- |
| I | Sepifilm LP 010 | 12 |
| II | Purified water | 88 |

The coatings are applied to the tablets by standard parameters and the dimensions of the tablets are measured.

| | Tablet dimensions | | |
| --- | --- | --- | --- |
| | Tablet height [mm] | Tablet width [mm] | Tablet length [mm] |
| Batch 1 uncoated | 6.0 | 9.5 | 19.1 |
| Batch 1 coated | 6.0 | 9.5 | 19.1 |
| Batch 2 coated | 6.0 | 9.5 | 19.1 |
| Batch 3 coated | 6.4 | 9.7 | 19.3 |

The tablets were tested in cassettes for two different dose-dispensing machines at Apoteket AB.

Cassettes YNS and BPM fitting a Tosho dose dispensing machine and an ATC cassette fitting a Baxter dose-dispensing machine were assembled and the tablets were tested.

All coated tablets were accepted for dose dispensing machines. Tablets from batch 1 uncoated were very dusty and therefore not ideal for this kind of equipment. The dust is avoided by applying a coating to the tablets.

Example 3

Testing of Round Tablets in Dose Dispensing Machines

The objective of this experiment was to test a round tablet in dose dispensing machines.

A final granulate according to batch 4 in Example 1 was manufactured and compressed into tablets using 13.95 mm round tablet tooling.

| Tablet dimensions | | |
|---|---|---|
| | Tablet diameter [mm] | Tablet height [mm] |
| Batch 4 | 14.02 | 7.98 |

The tablets were tested in cassettes for three different dose-dispensing machines at Apoteket AB.

The tablets were accepted for dose-dispensing machines. This was the case in spite of the max. recommended tablet dimensions for three different dose-dispensing machines:

| Distributor | Tablet diameter [mm] | Tablet height [mm] |
|---|---|---|
| Tosho | 14.0 | 9.4 |
| Baxter | 13.2 | 6.7 |
| Hyupshin | 14.0 | 7.0 |

The fact that tablets can be accepted for dose dispensing even though they exceed the limits recommended by the dose dispensing machine suppliers illustrates that a decision must be based on actual trials.

Example 4

Stability of Calcium Carbonate Tablets

This experiment was performed in order to investigate stability of crushing strength and disintegration time of tablets in open petri dishes at the conditions of 25° C./60% Relative Humidity. Tablets manufactured according to Example 1, batch 1 were compared to tablets manufactured in high shear mixer and containing sorbitol. Fluid bed based tablets were used as reference for the evaluation of crushing strength.

The manufacture of the high shear mixer based granulate containing sorbitol were done using the following design, composition and manufacture:

| Design | | | | |
|---|---|---|---|---|
| | Batch 1 | Batch 2 | Batch 3 | Batch 4 |
| Granulation fluid Amount [gram] | 385 | 385 | 307.5 | 307.5 |
| Granulation time [min] | 2 | 4 | 2 | 4 |
| Sorbitol mean particle size [μm] | 38 | 110 | 38 | 110 |

TABLE 4

| Composition | | |
|---|---|---|
| | Raw materials | Amounts Gram |
| I | Calcium carbonate (Scoralite) | 5352 |
| II | Sorbitol, 38 μm or 110 μm | 1648 |
| III | Povidone K 30 | 28.3 |
| IV | Purified water, high or low amounts | 307.5/385.0 |
| V | Starch 1500 | 231.2 |
| VI | Acesulfam Potassium | 4.28 |
| VII | Flavour Lemon | 32.1 |
| VIII | Magnesium stearate | 25.7 |

Manufacture:

III is dissolved in IV.

II is screened through a sieve 250 μm and mixed with I in a Fielder lab scale high shear mixer (1 min mixing time). The dissolved III is added by atomization and granulation is carried out for 2 or 4 minutes.

The wet granulate is dried in a lab scale fluid bed using an inlet air temperature of approx. 60° C. The granulate is dried to a maximum content of water less than 0.5% The rest of the excipient, V, VI and VIII are admixed and finally VIII is admixed. Tablet are compressed using a lab scale tablet press, Korsch PH 106, and capsule shaped punch design (9.4×18.9 mm)

The manufacture of the fluid bed based granulate was done according to Example 1 batch 4. Tablets were compressed using a Manesty B3B and a round 14 mm compound cup punch design.

The results of the investigation are shown in table 5 (for example 1 batch 1), in table 6 (for example 1 batch 4) and in FIGS. 1 and 2 for tablets containing sorbitol according to table 4.

TABLE 5

| Stability of tablets according to Example 1, batch 1 | | |
|---|---|---|
| Time [days] | Crushing strength [N] | Disintegration time [minutes] |
| 0 | 163 | 7.0 |
| 7 | 87 | 8.9 |
| 30 | 102 | 17.5 |
| 60 | 92 | 15.9 |
| 90 | 86 | 18.1 |

TABLE 6

| Stability of tablets according to example 1, batch 4 | |
|---|---|
| Time [days] | Cruching strength [N] |
| 0 | 87 |
| 1 | 32 |
| 2 | 30 |
| 4 | 33 |
| 7 | 30 |
| 14 | 31 |

For both the use of maltitol/xylitol and sorbitol tablets based on high shear mixer granulation tablets that are stable in accordance with the invention can be produced. However, tablets based on fluid bed granulation do not fulfil the requirements of the invention.

The invention claimed is:

1. A chewable, suckable and swallowable tablet, the tablet comprising one or more regularly shaped calcium-containing compound(s) as an active substance and sorbitol having a particle size D(v;0.5) below about 150 μm, which tablet has a porosity below 20% and has a crushing strength, when stored in an open petri dish at 25° C. and 60% relative humidity (RH) for one week or more, in a range from 40 to 150 N, wherein the tablet is suitable for dispensing via a dose-dispensing machine.

2. The tablet according to claim 1, wherein the one or more calcium-containing compound is in the form of crystals having a specific surface area below 1.5 m²/g.

3. The tablet according to claim 1, wherein the concentration of the sorbitol is at least 5% w/w.

4. The tablet according to claim 1, wherein the sorbitol has a mean particle size of at the most 150 μm.

5. The tablet according to claim 1, which has an acceptable taste and mouthfeel when tested by a professional/skilled sensory test panel of at least 6 test persons.

6. The tablet according to claim 1, wherein the tablet is stable when stored in a closed container at 25° C. and 60% RH for 6 months or more.

7. The tablet according to claim 1, wherein the tablet is stable towards storage in a closed container at 30° C. and 65% RH for 2 months or more.

8. The tablet according to claim 1, wherein the tablet is stable towards storage in a closed container at 40° C. and 75% RH for 1 month or more.

9. The tablet according to claim 1, wherein the crushing strength of the tablets, when stored in open petri dishes for at least 1 week at 25° C. and 60% RH, at the most changes 50% during a time period that starts after 5 days of storage and runs during the remaining storage period.

10. The tablet according to claim 1, wherein the friability of the tablets is at the most 5% during the storage period.

11. The tablet according to claim 1, wherein the friability of the tablets, when stored in open petri dishes at 25° C. and 60% RH for at least 1 week, at the most changes 50% during a time period that starts after 5 days of storage and runs during the remaining storage period.

12. The tablet according to claim 1, wherein the appearance of the tablet as determined by visual inspection does not significantly change during the storage period and wherein the storage period is at least 1 week.

13. The tablet according to claim 1, wherein water sorption of the tablet is at the most 5% at 25° C. and 60% RH.

14. The tablet according to claim 1, wherein water sorption of the tablet at 25° C. and 60% RH at the most changes 50% during the storage period and wherein the storage period is at least 1 week.

15. The tablet according to claim 1, wherein the disintegration time determined according to the European Pharmacopoeia (Ph. Eur.) is at the most 30 min.

16. The tablet according to claim 1, wherein the disintegration time at the most changes 50% during a time period that starts after 5 days of storage and runs during the remaining storage period, and wherein the storage period is at least 1 week.

17. The tablet according to claim 1, wherein at least 50% w/w of the calcium-containing compound is released within at the most 2 hours.

18. The tablet according to claim 1, wherein the dissolution time measured as the time for 60% w/w of the calcium-containing compound to be released in a dissolution test according to USP at the most changes 50% during a time period that starts after 5 days of storage and runs during the remaining storage period, wherein the storage period is at least 1 week.

19. The tablet according to claim 1, wherein the calcium-containing compound is a calcium salt.

20. The tablet according to claim 19, wherein the calcium salt is calcium carbonate.

21. The tablet according to claim 1 comprising one or more second calcium-containing compounds selected from the group consisting of bisglycino calcium, calcium acetate, calcium carbonate, calcium chloride, calcium citrate, calcium citrate malate, calcium cornate, calcium fluoride, calcium glubionate, calcium gluconate, calcium glycerophosphate, calcium hydrogen phosphate, calcium hydroxyapatite, calcium lactate, calcium lactobionate, calcium lactogluconate, calcium phosphate, calcium pidolate, calcium stearate and tricalcium phosphate.

22. The tablet according to claim 1, wherein the amount of the calcium-containing compound corresponds to from about 100 to about 1000 mg Ca.

23. The tablet according to claim 1, wherein the total concentration of the one or more calcium-containing compound is in a range of from about 40% to about 99% w/w.

24. The tablet according to claim 1 containing from about 60% to about 95% w/w of the calcium-containing compound and from about 5% to about 40% w/w of sorbitol, provided that the sum does not exceed 100% w/w.

25. The tablet according to claim 1 containing from about 60 to about 94% of the calcium-containing compound, from about 5 to about 35% w/w of sorbitol and from about 1 to about 15% w/w of one or more pharmaceutically acceptable excipients and/or active substances, provided that the sum of ingredients amounts to 100% w/w.

26. The tablet according to claim 1 further comprising one or more pharmaceutically acceptable excipients or additives, or one or more therapeutically, prophylactically and/or diagnostically active substances.

27. The tablet according to claim 1 further comprising vitamin D or a vitamin K or Magnesium.

28. The tablet according to claim 27, wherein the content of D vitamin in the tablet at the most changes 20% w/w during the storage period, wherein the storage period is at least 1 week.

29. The tablet according to claim 27, wherein at least 50% w/w of the D vitamin is released within at the most 2 hours.

30. The tablet according to claim 27, wherein the dissolution time-measured as the time for 60% w/w of the D vitamin of the tablet to be released in a dissolution test according to USP—at the most changes 50% during a time period that starts after 5 days of storage and runs during the remaining storage period.

31. The tablet according to claim 1, wherein the tablet is coated with film-coating.

32. The tablet according to claim 31, wherein the coating is applied in an amount that corresponds to an increase in weight of the tablet of at the most 2% based on the weight of the uncoated tablets.

33. The tablet according to claim 1 in the form of a chewable, suckable and swallowable tablet having a disintegration time according to the European Pharmacopoeia (Ph. Eur.) of at most 15 minutes.

34. The tablet according to claim 33, which has an acceptable taste with respect to sweetness, flavour and chalkiness when tested by a professional/skilled sensory test panel of at least 6 persons.

35. A solid dosage form according to the tablet of claim 1, wherein the tablets have a shape and dimensions of:
- a maximum length of 19.3 mm;
- a maximum width of 9.7 mm; and
- a maximum height of 7.2 mm, and a weight below 1750 mg for a content of elementary calcium of 500 mg.

36. The tablet according to claim 1 further comprising a sweetener selected from the group consisting of dextrose, fructose, glycerin, glucose, isomalt, lactitol, lactose, maltitol, maltose, mannitol, sorbitol, sucrose, tagatose, trehalose, xylitol, alitame, aspartame, acesulfam potassium, cyclamic acid, cyclamate salt, neohesperidine dihydrochalcone, thaumatin, saccharin, saccharin salt, sucralose and mixtures thereof.

37. A cassette for dose-dispensing comprising a tablet as defined in claim 1.

\* \* \* \* \*